(12) United States Patent
Roberts et al.

(10) Patent No.: US 11,052,266 B2
(45) Date of Patent: Jul. 6, 2021

(54) METHOD AND APPARATUS FOR BEAM ENERGY MEASUREMENT

(71) Applicant: Elekta Limited, West Sussex (GB)

(72) Inventors: David Anthony Roberts, West Sussex (GB); Janusz Harasimowicz, Redhill (GB); Peter Doherty, West Sussex (GB); Mark Strangeman, West Sussex (GB)

(73) Assignee: Elekta Limited, West Sussex (GB)

( * ) Notice: Subject to any disclaimer, the term of this patent is extended or adjusted under 35 U.S.C. 154(b) by 20 days.

(21) Appl. No.: 16/276,679

(22) Filed: Feb. 15, 2019

(65) Prior Publication Data
US 2020/0023204 A1 Jan. 23, 2020

(30) Foreign Application Priority Data
Feb. 19, 2018 (GB) ..................................... 1802646

(51) Int. Cl.
*A61N 5/10* (2006.01)
*G01T 1/185* (2006.01)
*G01T 1/29* (2006.01)

(52) U.S. Cl.
CPC ......... *A61N 5/1067* (2013.01); *A61N 5/1075* (2013.01); *G01T 1/185* (2013.01); *G01T 1/2914* (2013.01); *A61N 5/1071* (2013.01)

(58) Field of Classification Search
None
See application file for complete search history.

(56) References Cited

U.S. PATENT DOCUMENTS 2,566,684 A * 9/1951 Tobias ...................... G01T 1/29
250/385.1
4,131,799 A * 12/1978 Stieber ...................... G01T 1/29
250/385.1
4,347,547 A * 8/1982 Gibson ...................... G01T 1/29
250/385.1

(Continued)

FOREIGN PATENT DOCUMENTS

GB 958240 5/1964
GB 1463891 2/1977

(Continued)

OTHER PUBLICATIONS

International Search Report for corresponding GB Application No. 1802646.8, filed Aug. 22, 2018 (dated May 11, 2018).

*Primary Examiner* — Thomas R Artman
(74) *Attorney, Agent, or Firm* — Finnegan, Henderson, Farabow, Garrett & Dunner LLP (57) ABSTRACT

Apparatus for measuring radiation beam energy output from a radiation beam source, comprising a first beam energy sensor at a first distance from the radiation beam source along the radiation beam axis; a second beam energy sensor located at a second distance from the radiation beam source along the radiation beam axis; and an energy absorbing layer, for example a layer that removes a part of the low energy content of the beam or a layer that absorbs at least 1% of the beam energy, located between the first and second sensors, and positioned such that radiation passing through the first sensor also passes through the energy absorbing layer before entering the second sensor.

17 Claims, 7 Drawing Sheets

(56) References Cited

U.S. PATENT DOCUMENTS

| | | | | |
|---|---|---|---|---|
| 4,427,890 A * | 1/1984 | Taumann | ............... | H01J 47/02 |
| | | | | 250/385.1 |
| 4,803,368 A | 2/1989 | Barthelmes | | |
| 4,855,598 A | 8/1989 | Ohgoda et al. | | |
| 4,975,585 A * | 12/1990 | Asai | ............... | G01T 1/185 |
| | | | | 250/374 |
| 5,672,878 A * | 9/1997 | Yao | ............... | G01T 1/185 |
| | | | | 250/385.1 |
| 5,760,404 A * | 6/1998 | Rannikko | ............... | G01T 1/185 |
| | | | | 250/374 |
| 9,980,697 B2 * | 5/2018 | Dujmic | ............... | G01N 23/083 |
| 10,183,181 B2 * | 1/2019 | Kawrykow | ............... | A61B 5/055 |
| 10,821,304 B2 * | 11/2020 | Kawrykow | ............... | G01T 1/185 |
| 2009/0200476 A1 * | 8/2009 | Brusasco | ............... | A61N 5/1048 |
| | | | | 250/370.07 |
| 2012/0104270 A1 * | 5/2012 | Marchand | ............... | G01T 1/2935 |
| | | | | 250/389 |
| 2017/0021198 A1 | 1/2017 | Kawrykow et al. | | |
| 2017/0184737 A1 * | 6/2017 | Dujmic | ............... | G01V 5/0016 |
| 2019/0240511 A1 * | 8/2019 | Kawrykow | ............... | G01T 1/29 |
| 2020/0023204 A1 * | 1/2020 | Roberts | ............... | A61N 5/1075 |

FOREIGN PATENT DOCUMENTS

| | | | | |
|---|---|---|---|---|
| WO | WO-8103084 A1 * | 10/1981 | ............... | H05H 7/00 |
| WO | WO 2014-117852 | 8/2014 | | |
| WO | WO 2016-007599 | 1/2016 | | |

* cited by examiner

METHOD AND APPARATUS FOR BEAM ENERGY MEASUREMENT

CROSS-REFERENCE TO RELATED APPLICATION

This application claims the benefit and priority of prior United Kingdom Patent Application No. 1802646.8, filed on Feb. 19, 2018, the entire contents of which are incorporated by reference herein.

FIELD OF THE INVENTION

The present invention relates to methods and apparatus for measurement of the energy of a radiation beam, such as an x-ray beam in a radiotherapy apparatus.

BACKGROUND ART

International Standards IEC 60601-2-1:2009 and IEC 60601-2-1:2009/A1:2014 set forth particular requirements for safety and essential performance of medical equipment utilising electron accelerators for the generation of x-ray beams in the MeV energy range. The measurement of beam energy is important for safe operation of such equipment. One requirement is that two sensors for measuring beam energy be provided to allow for redundancy in case on sensor fails. Another requirement is that operation of the equipment should be ceased if the beam energy varies outside predetermined limits.

US 2017/0021198 discloses an ion chamber for use in measuring the beam energy in a radiotherapy system, including a magnetic resonance imaging system. Ion chambers are well-known for use in beam energy monitoring. They operate by converting incoming radiation into electrons and then measuring the current produced by these electrons to derive the beam energy. In addition to safety requirements, beam energy measurements are useful in radiotherapy systems for proper control of radiation dosage. Such control may require more accurate measurement of beam energy that is required for safe operation.

In addition to accuracy, it is also useful to be able to recognize different types of beam failure and to be able to discriminate between sensor failure and beam failure.

To be effective, a suitable sensor should sample the whole beam while still allowing the major part of the beam to pass through so as to be useful for treatment of the patient. Therefore, the sensor may at most only attenuate the beam by a few percent. It is from this small percentage of the beam, that any energy changes must be detected.

This invention attempts to address some of these challenges.

SUMMARY OF THE INVENTION

A first aspect of the invention provides a method of determining a change in radiation beam energy output from a radiation beam source, comprising making a first beam energy measurement at a first time and at a first distance from the radiation beam source along the radiation beam axis; making a second beam energy measurement at the first time at a second distance from the radiation beam source along the radiation beam axis, wherein the second distance is greater than the first distance, and wherein the beam has passed through an energy absorbing layer, for example a layer that absorbs at least 1% of the beam energy, between the first and second distances; making a third beam energy measurement at a second time at the first distance; making a fourth beam energy measurement at the second time at the second distance, wherein the beam has passed through the energy absorbing layer; and measuring changes between the first, second, third, and fourth beam energy measurements, and determining the change in beam energy from the first time to the second time using the measured changes.

Comparing energy measurements across the energy absorbing layer emphasises energy changes due to changes in the beam output.

The first and third beam energy measurements can be made in a central region including the beam axis, and the second and fourth beam energy measurement can be made in a peripheral region surrounding but not including the central region. The method can further comprise making a fifth beam energy measurement at a first time at the first distance, and a sixth beam energy measurement at a second time at the first distance, wherein the fifth and sixth beam energy measurements are in the peripheral region; making a seventh beam energy measurement at the first time at the second distance, wherein the beam has passed through the energy absorbing layer, and an eighth beam energy measurement at the second time at the second distance, wherein the beam has passed through the energy absorbing layer, wherein the seventh and eighth measurements are in the central region; and measuring changes between the first, second, third, fourth, fifth, sixth, seventh, and eighth beam energy measurements, and determining the change in beam energy from the first time to the second time using the measured changes.

The beam energy varies with distance from the beam axis. By making separate measurement on the central and peripheral regions, changes in source output can be detected.

A second aspect of the invention provides apparatus for measuring radiation beam energy output from a radiation beam source, comprising a first beam energy sensor at a first distance from the radiation beam source along the radiation beam axis; a second beam energy sensor located at a second distance from the radiation beam source along the radiation beam axis; and an energy absorbing layer, for example a layer that removes a part of the low energy content of the beam or a layer that absorbs at least 1% of the beam energy, located between the first and second sensors, and positioned such that radiation passing through the first sensor also passes through the energy absorbing layer before entering the second sensor.

The energy absorbing layer can have an energy absorption that is at least that of 2 mm of stainless steel.

Each sensor can comprise a body defining a chamber, and upper and lower cover layers through which the radiation beam must pass for energy measurement. The energy absorbing layer can be separate from the cover layers or can be integral with one or more of the cover layers.

Each sensor can comprise an ion chamber, such as an ion chamber that comprises a body enclosing a signal electrode and polarising electrodes disposed on either side of the signal electrode. Each signal electrode can comprises a first electrode region configured, in use, to sample a central region of a radiation beam including the beam axis, and second electrode region at least partially surrounding the first electrode region and configured, in use, to sample a peripheral region surrounding but not including the central region. The ratio of the areas of the first and second electrode regions of the first sensor can be different to the corresponding ratio of the second sensor. For example, the area of the first electrode regions of the first sensor can be less than the area of the second electrode region of the first sensor; and the areas of the first and second electrode regions of the second sensor are approximately equal.

The sensing area of each ion chamber can be selected according to the shape of the radiation beam. In one example, this can be substantially rectangular for accurately monitoring a rectangular section beam.

A third aspect of the invention provides radiotherapy system comprising a radiation generation system including an electron accelerator x-ray source for producing a beam of x-rays for treating a patient, and an apparatus according to the second aspect positioned between the source and a treatment location of the patient.

The radiotherapy system can, further comprise a gantry on which the radiation generation system is mounted, the gantry being rotatable around the treatment location. The gantry can be mounted for rotation through more than 360° around the treatment location.

The radiotherapy system can also further comprise a magnetic resonance imaging system for imaging the patient at the treatment location during treatment with the beam of x-rays.

A fourth aspect of the invention provides a method of operating a radiotherapy system according to the third aspect, the method comprising operating the source to generate a beam of x-rays; and operating the apparatus for measuring radiation beam energy output from the source in accordance with a method according to the first aspect.

The method can further comprise automatically ceasing operation of the source when the determined change in beam energy exceeds a predetermined value.

Further aspects of the invention may be apparent from the following description.

BRIEF DESCRIPTION OF THE DRAWINGS

The invention will now be described by way of example and with reference to the accompanying figures in which.

DETAILED DESCRIPTION OF THE EMBODIMENTS

Figure 1:
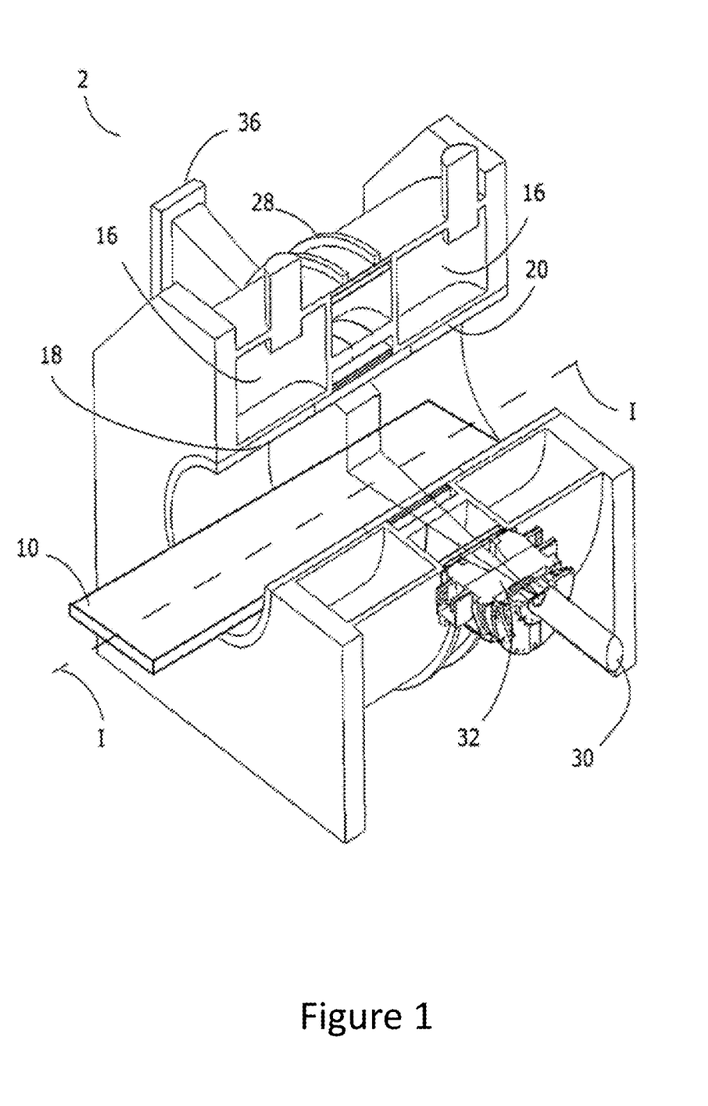
FIG. 1 shows a radiotherapy system including a magnetic resonance imaging system.

FIG. 1 shows a system comprising a radiotherapy apparatus and a magnetic resonance imaging (MRI) apparatus, such as is described in EP 2359905.

The system includes a couch 10, for supporting a patient in the apparatus. The couch 10 is movable along a horizontal, translation axis (labelled "I"), such that a patient resting on the couch is moved into the radiotherapy and MRI apparatus. as described in WO 2009/007737.

The system 2 also comprises an MRI apparatus, for producing real-time images of a patient positioned on the couch 10. The MRI apparatus includes a primary magnet 16 which acts to generate the primary magnetic field for magnetic resonance imaging. The magnetic field lines generated by the magnet 16 run substantially parallel to the central translation axis I. The primary magnet 16 comprises one or more coils with an axis that runs parallel to the translation axis I. The one or more coils may be a single coil or a plurality of coaxial coils of different diameter, as illustrated. The coil(s) in the primary magnet 16 is arranged such that a central window of the magnet 16 is free of coils. The magnet 16 may further comprise one or more active shielding coils, for generating a magnetic field outside the magnet 16 of approximately equal magnitude and opposite polarity to the primary magnetic field. The more sensitive parts of the system 2, such as the accelerator, are positioned in this region outside the magnet 16 where the magnetic field is cancelled, at least to a first order. The MRI apparatus further comprises two gradient coils 18, 20, which generate the gradient magnetic field that is superposed on the primary magnetic field. These coils 18, 20 generate a gradient in the resultant magnetic field that allows spatial encoding of the protons so that their position can be determined from the frequency at which resonance occurs (the Larmor frequency). The gradient coils 18, 20 are positioned around a common central axis with the primary magnet 16, and are displaced from one another along that central axis. This displacement creates a gap, or window, between the two coils 18, 20. In an embodiment where the primary magnet 16 also comprises a central window between coils, the two windows are aligned with one another.

An RF system transmits radio signals at varying frequencies towards the patient, and detects the absorption at those frequencies so that the presence and location of protons in the patient can be determined. The RF system may include a single coil that both transmits the radio signals and receives the reflected signals, dedicated transmitting and receiving coils, or multi-element phased array coils, for example. Control circuitry controls the operation of the various coils 16, 18, 20 and the RF system, and signal-processing circuitry receives the output of the RF system, for generating images of the patient supported by the couch 10.

The system 2 further comprises a radiotherapy apparatus 6 which delivers doses of radiation to a patient supported by the couch 10. The majority of the radiotherapy apparatus 6, including at least a radiation generation system including source of radiation 30 (e.g. an x-ray source) and a multi-leaf collimator (MLC) 32, is mounted on a chassis or gantry 28. The chassis 28 is continuously rotatable around the couch 10 when it is inserted into the treatment area, powered by one or more chassis motors. The radiotherapy apparatus further comprises control circuitry, which controls the radiation source 30, the MLC 32 and the chassis motor.

The radiation source 30 is positioned to emit radiation through the window defined by the two gradient coils 18, 20, and also through the window defined in the primary magnet 16. The source 30 emits a divergent beam of radiation. The radiation beam is collimated to a rounded corner rectangular section with appropriate shielding prior to arrival at the MLC 32. The radiation beam is relatively narrow in the axial direction, and is relatively wide in azimuthal direction (both with respect to the axis of rotation of the chassis). The beam can have a substantially rectangular cross-section. Thus, the beam takes a "fan" shape that is suited to the geometry of the system 2, in which two gradient coils 18, 20 are displaced from one another in order to allow the radiation access to the patient. A fan-shaped beam provides substantial radiation to the patient through the narrow window, meaning that the gradient coils 18, 20 can be placed closer together than with conventional integrated radiotherapy/imaging systems. This allows the gradient coils 18, 20 to generate stronger gradient fields than would otherwise be the case, increasing the quality of the images obtained by the MRI apparatus.

Figure 2:
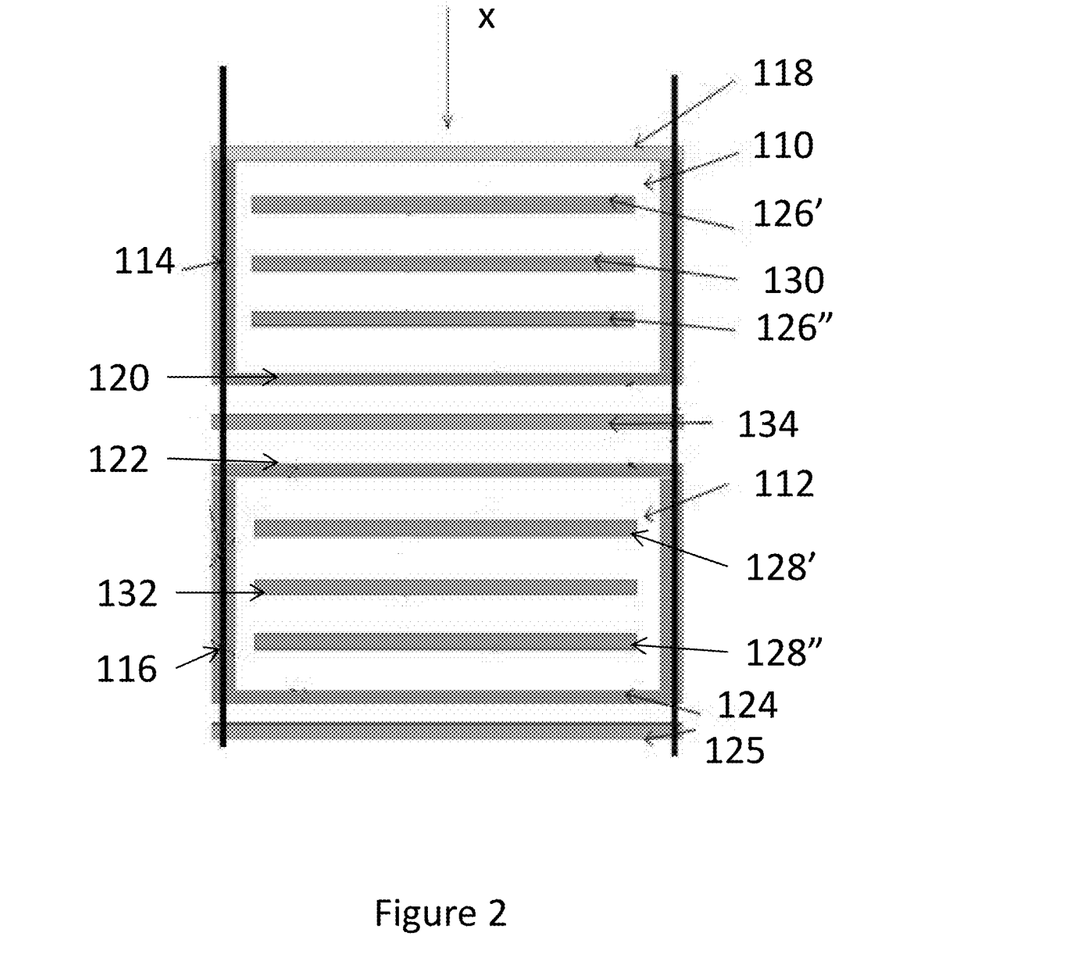
FIGS. 2 and 3 show schematic and perspective cross-sections through a sensor.
Figure 3:
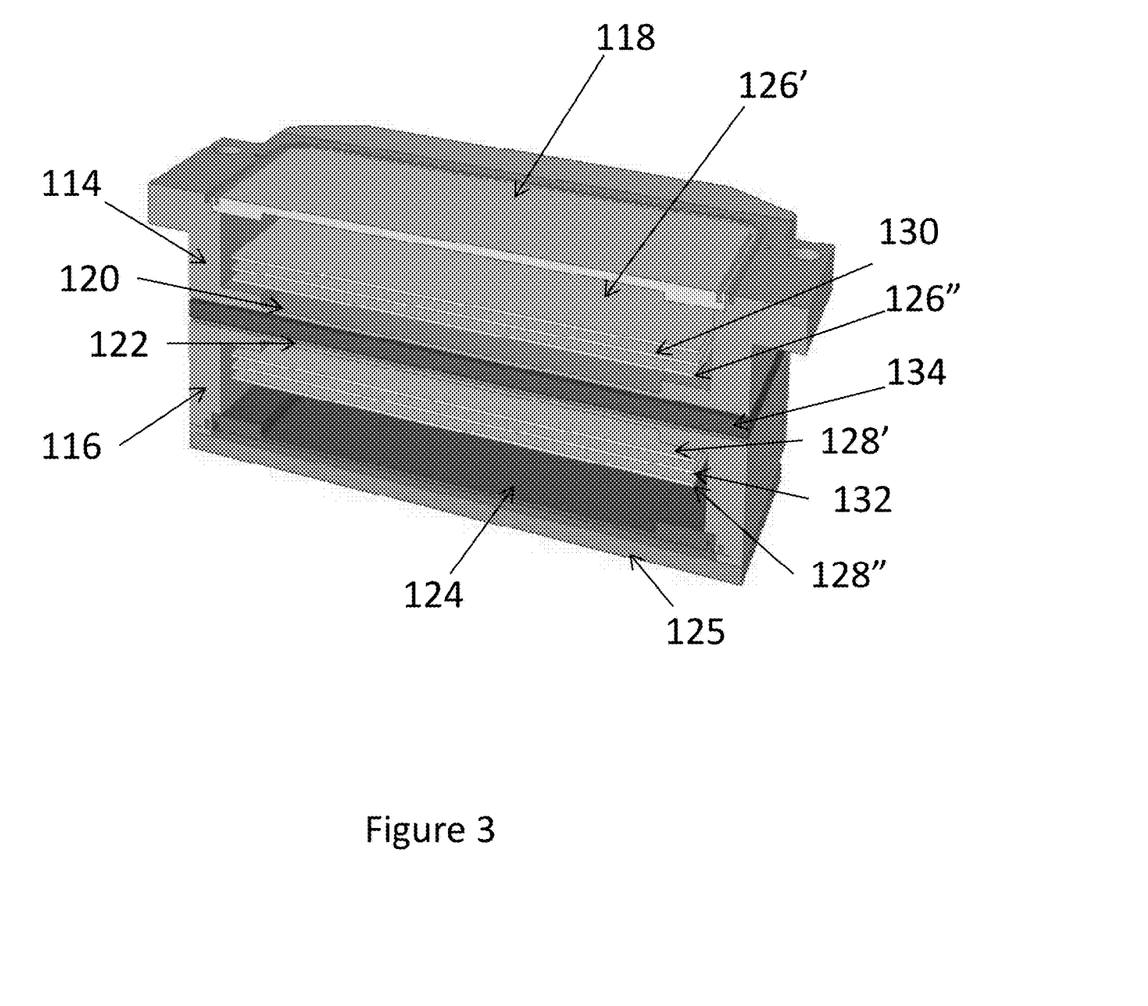

FIG. 2 shows a schematic section through a sensor according to an embodiment of the invention. FIG. 3 shows a perspective view of the sensor of FIG. 2. The energy monitor of FIGS. 2 and 3 comprises two independent detection chambers 110, 112, each of which defines a separate sensor. Each chamber 110, 112 is delimited by a housing comprising a wall 114, 116. The upper chamber is closed by a build-up plate 118 which defines a window through which the radiation beam x enters the chamber 110. A lower cover plate 120 closes the lower end of the upper chamber 110. The lower chamber 112 has a similar structure. In this case, cover plates 122,124 close the upper and lower ends of the chamber 112, the upper cover plate 122 serving as a window through which the radiation beam enters the lower chamber 112. A backscatter plate 125, for example an aluminium plate, can be provided below the lower cover plate 124.

In use, the upper chamber 110 is installed so as to be centred on the beam axis x closer to the source, and the lower chamber 112 is installed so as to be centred on the beam axis x closer to the to the patient as will be described in further detail below.

There are three parallel electrode plates in each chamber 110, 112, two polarizing electrodes 126', 126", 128', 128" disposed on either side of a signal electrode 130, 132. Applying a voltage across the electrodes creates an electric field between adjacent electrodes. When the gas in the chamber is ionised by the beam, ion-pairs are created which drift to the electrodes under the influence of the electric field. This generates an ionisation current from the signal electrode which is measured.

An energy discrimination plate 134 is located between the chambers 110, 112 such that any radiation that has passed through the upper chamber 110 must pass through the energy discrimination plate before entering the lower chamber 112. The energy discrimination plate absorbs some of the beam energy such that the response from the lower chamber 112 is different from that of the upper chamber. For example, the energy discrimination plate may absorb at least 1% of the beam energy. This can be achieved by providing a stainless steel plate of at least 2 mm thickness between the two chambers 110, 112. This is in addition to any contribution from the lower cover plate 120 and the upper cover plate 122.

Figure 4:
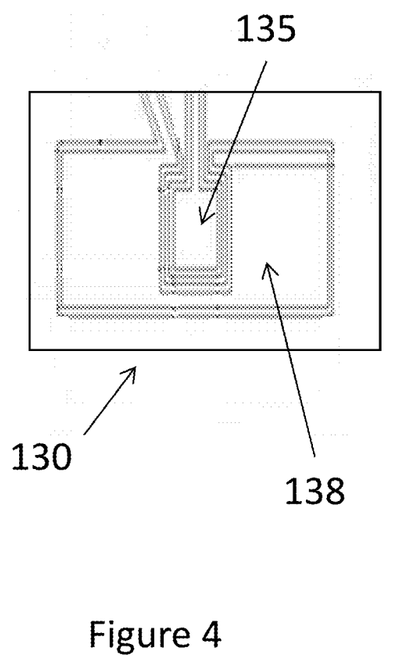
FIG. 4 shows an upper signal electrode.
Figure 5:
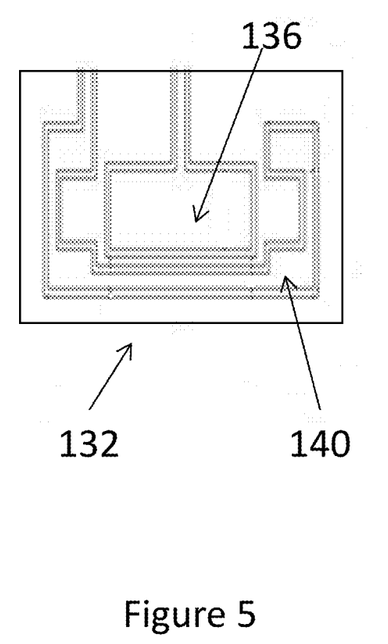
FIG. 5 shows a lower signal electrode.

FIGS. 4 and 5 each show further details of the signal electrodes 130, 132 each having two sensing electrode areas defined thereon: central electrodes 135, 136; and peripheral electrodes 138, 140. The central electrodes define a sensing area that is centred on the beam axis. The peripheral electrodes define a sensing are that substantially surrounds the central electrode. The central and peripheral electrodes are not in electrical contact with each other and so provide measurements that are independent of each other.

As can be seen, the shapes and sizes of these areas are different for the upper and lower sensors. The electrode 130 in the upper chamber 110 has a relatively smaller central electrode 135, and a larger peripheral electrode 138. For example, the ratio of the central area to the peripheral area is less than 1, such as 1:9. In the lower chamber 112, the central electrode 136 is relatively larger and the peripheral electrode 140 smaller. In this case, the ration of areas is close to 1:1. For comparison, the central electrode 136 of the lower chamber 112 is about three times larger than the corresponding electrode 135 in the upper chamber 110, while the peripheral electrode 138 of the upper chamber 110 is about three times larger than the corresponding electrode 140 in the lower chamber 112. The figures show one side of each electrode. As the sensing electrode detects from both sides, the actual sensing area is twice that shown in the figures.

In this way, each sensor will have different on-axis and peripheral sensitivity, and the respective sensitivities of the upper and lower on-axis measurements, and the upper and lower peripheral measurements will also be different. Accordingly, a comparison of the upper and lower measurements can be used to identify beam energy changes more easily, particularly as measurements in the peripheral region are more sensitive to changes in beam energy. Also, the presence of the energy discrimination plate 134 means that any variation in the upper sensor measurement arising from a change in the beam, such as a shift from a photon beam to an electron beam due to failure of the target in the source 30 resulting in high energy electrons entering the upper chamber 110 will not be reflected in the measurement from the lower chamber 112, thus allowing better identification of this type of failure.

The four corners of the peripheral electrode 140 in the lower chamber 112 can be relatively enlarged and positioned so that they do not overlap with at least one pair of sides of the central electrode 136. The results in greater separation of the sensed areas of the beam. As will be explained below, this can assist in detecting beam energy changes.

The polarising electrodes 126, 128 have substantially rectangular shapes and are sized so that the signal electrodes 130, 132 lie completely within the coverage of the polarising electrodes (other shapes and/or sizes can be used as appropriate).

By providing separate central and peripheral electrodes, each sensor chamber can provide a profile measurement indicative of the variation in beam energy with distance from the beam axis. The energy discrimination plate has the effect of reducing the peripheral measurement in the lower chamber 112 compared to the on-axis measurement, meaning that the lower chamber 112 will produce a different energy distribution profile to the upper chamber 110. Furthermore, the different arrangement of electrode areas in the upper and lower chambers emphasises this effect. the upper chamber measurement is weighted more to the periphery (flatter curve), whereas the lower chamber measurement is weighted more to the centre (sharper curve). A change in beam energy will therefore not only affect the total energy measured in each chamber, but also the ratio between central and peripheral energy measurements. These changes will be different if the change in energy is due to normal variation of the source output, or due to some other cause of change, e.g. target failure, as is explained further below.

Figure 6:
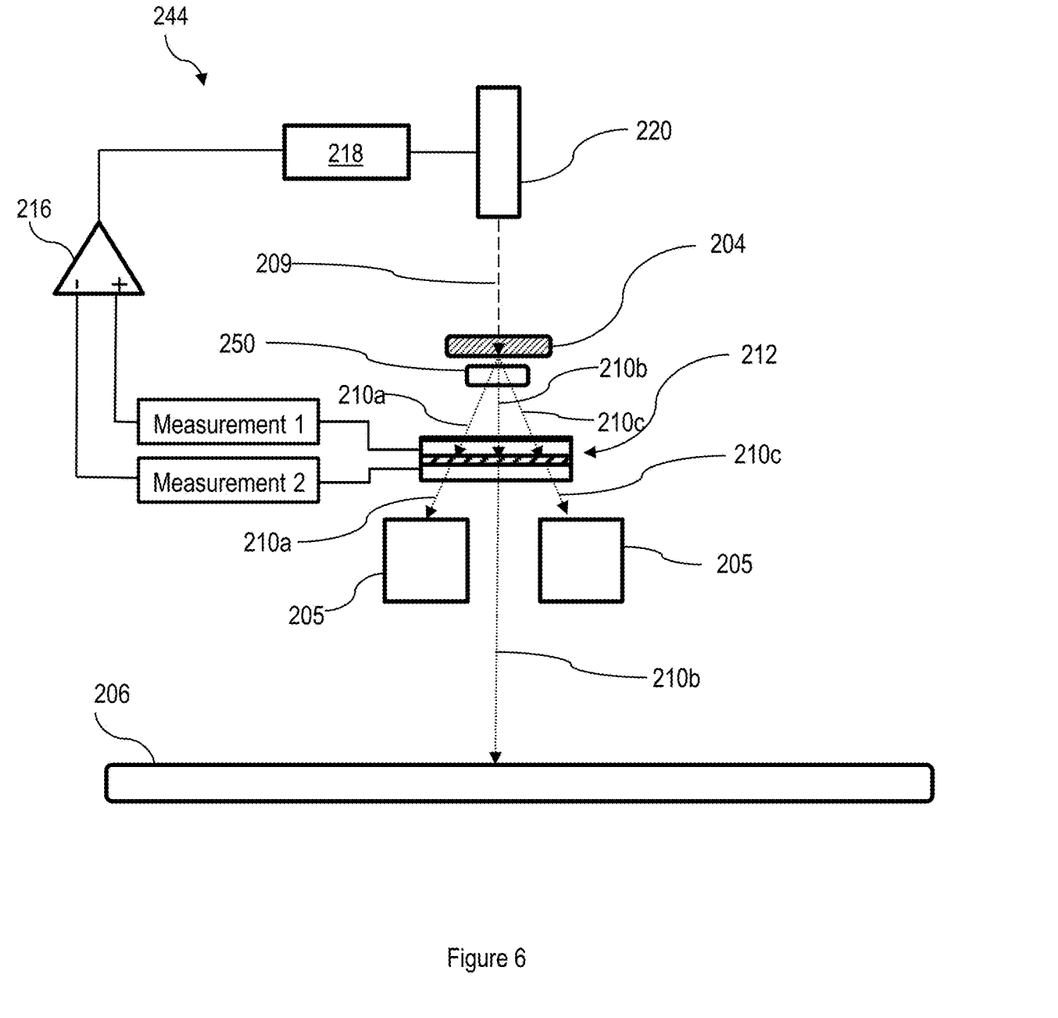
FIGS. 6 and 7 show schematics of a radiotherapy system including the sensor of FIGS. 2 and 3.

FIG. 6 is a schematic diagram of a radiotherapy system incorporating the sensor apparatus described above. The radiotherapy system 244 comprises an accelerator 220, which produces a beam of electrons 209 (shown as a dashed line indicating the beam axis), an X-ray target 204, an optional beam filter apparatus 250, a beam collimation apparatus 205 and a patient support surface 206. The radiotherapy system further comprises a detector apparatus 212 (as per FIGS. 2 and 3), and a radiotherapy system control system 218 including a comparator 216. The comparator provides a comparison of the outputs of the first detector and second detector, of the detector apparatus 212 to the radiotherapy system control system 218. The radiotherapy system control system 218 may be electrically coupled to the accelerator 220, thereby to allow the radiotherapy system control system 218 to control a radiation beam generated by the accelerator 220.

In the system 244, the beam of electrons 209 from the accelerator 220 travel towards the X-ray target 204. The X-ray target 204 is typically a piece of molybdenum, copper, tungsten, tungsten alloy or a combination thereof. Upon interaction with the X-ray target 204, the majority of electrons get absorbed by the target, but a few will be converted into high-energy X-rays 210a, 210b, 210c (shown as dotted lines) produced over a range of angles from the target 204, the angular distribution and beam shape depending on the incident electron energy. The majority of these X-rays then travel through the beam filter apparatus 250 and primary collimation system (not shown). Types of beam filter include flattening filters, or beam scattering filters, for example, although it is understood that the beam filter apparatus 250 is not essential to the functioning of the system 244 and may be omitted entirely if desired. The X-rays 210a, 210b, 210c then travel onwards towards the detector apparatus 212 which, as mentioned above, is assumed to comprise two ion chambers. Upon reaching the detector apparatus 212, a small proportion of the X-rays will interact with the build-up plate 118 (shown in FIGS. 2 and 3), and produce electrons (not shown). These electrons will then travel through the detector chambers, ionising the gas within and creating free ions that move towards the electrodes under the effect of the electric field, and recorded as a current, proportional to the dose passing through the detector(s).

Those X-rays which do not get converted into electrons continue through the detector apparatus 212, towards a beam collimation apparatus 205. The beam collimation apparatus 205 could be, for example, jaws from a diaphragm, or leaves from a multi-leaf collimator or iris collimator, or any other means for shaping or collimating a beam of X-rays. X-rays 210a, 210c whose beam paths bring them into contact with the beam collimation apparatus 205 will be blocked, whereas X-rays 210b travelling between the beam collimation apparatus will continue onwards a patient support surface 206.

Dose rate measurements from the first detector and the second detector are relayed to the comparator 216, which is configured to compare the measurements from the first and second detectors. In the event the measurement from the first detector is different from the measurement from the second detector by a predetermined amount, for example 20%, a beam failure can be indicated. Moreover, in some cases, the signal can indicate that the likely cause of the change in beam failure is failure of the X-ray target 204. This signal can be used to diagnose a beam fault within a radiotherapy system. The signal can optionally be used as an additional safety interlock. For example, upon receiving the signal, the radiotherapy system control system 218 can deactivate the radiation beam. For example, the radiotherapy system control system 218 could deactivate the accelerator 220, thus preventing further radiation from being produced.

Figure 7:
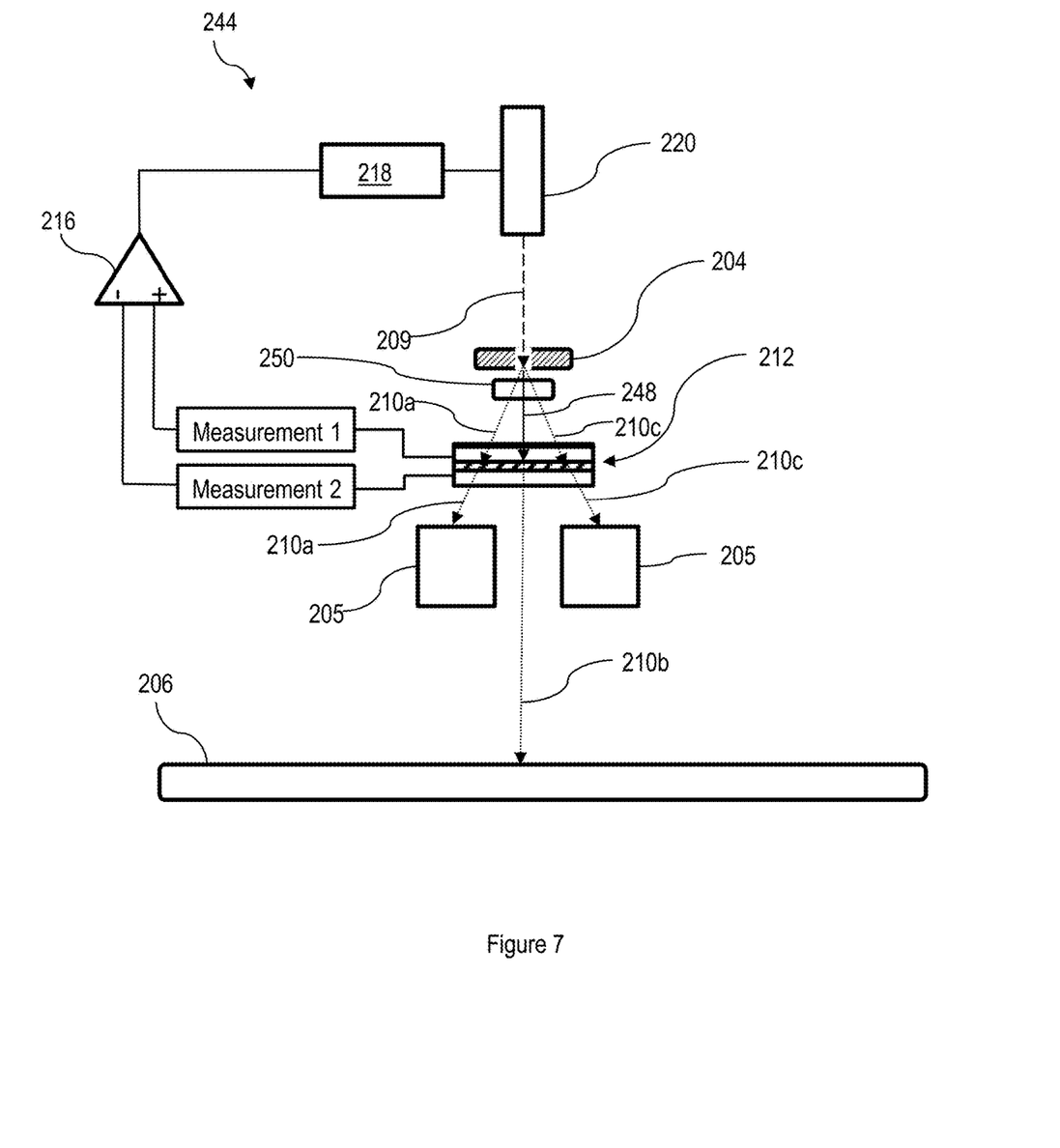

FIG. 7 shows the radiotherapy system 244 of FIG. 6 when the X-ray target 204 has mechanically failed. In this state, the target will still create X-rays 210a, 210b, 210c (shown as dotted lines), but a proportion of the electrons 248 (shown as a solid line) in the electron beam 209 will pass through the target 204, and onwards towards the detector apparatus 212. A small percentage of these electrons 248 will be blocked by the build-up plate, but the majority will continue through the plate into the detector apparatus 212. These electrons 248 will ionise the gas within the first detector, creating free charges which are used to determine the dose passing through the detector as previously described. Because the X-ray target 204 has failed, the number of electrons travelling through the first detector is much greater than normal, and so the dose rate determined from the current measured by the first detector is much higher. However, unlike X-rays 210a, 210b, 210c, very few of these electrons will be able to penetrate through the energy discrimination layer, and so the dose rate determined from the current measured by the second detector will be less affected by the failure of the target. By analysing the difference between the dose measured in the first chamber and the dose measured in the second chamber, one can quickly determine whether a beam failure was caused by the X-ray target 204 failing.

Figure 8:
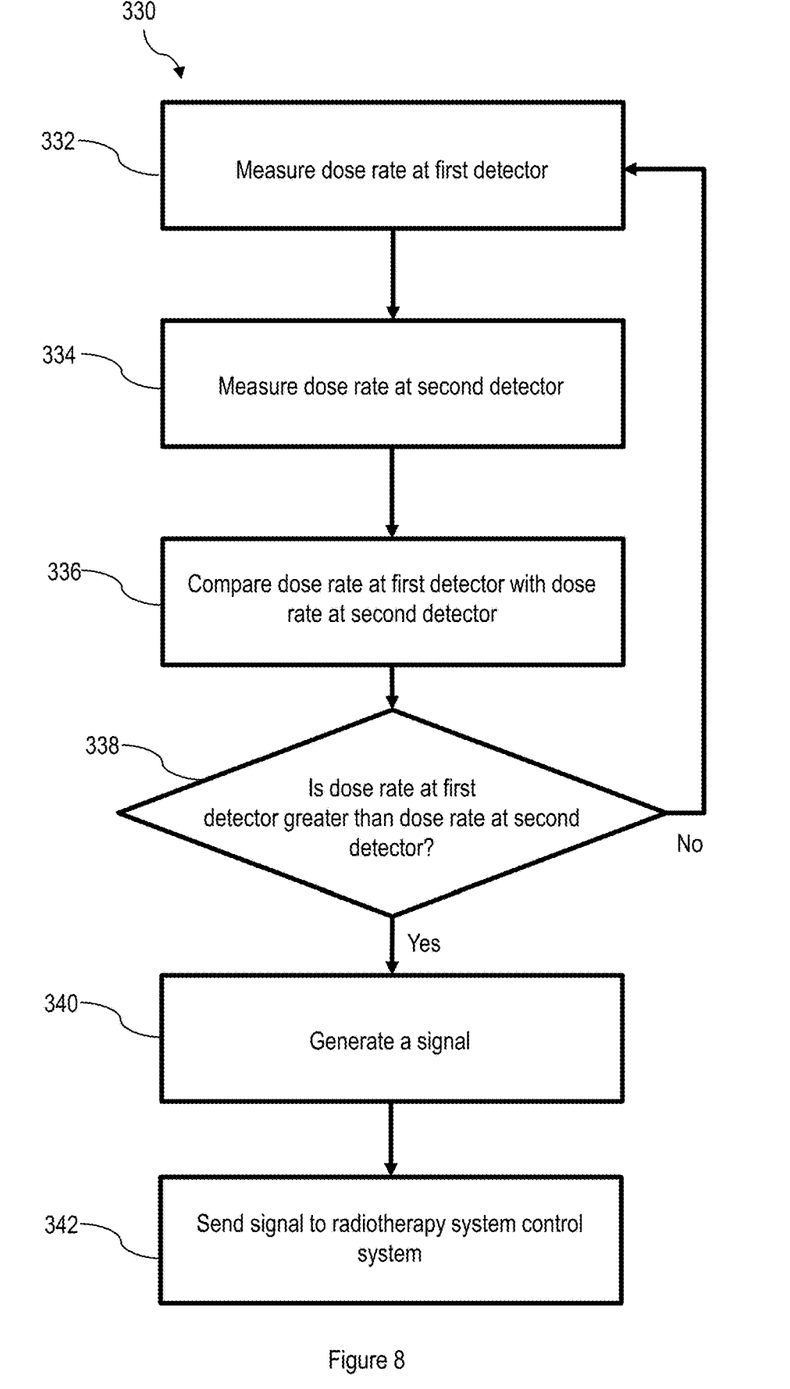
FIG. 8 shows a flow diagram outlining method steps.

FIG. 8 is a flow chart of a method 330 for detecting failure of an X-ray target 204. At step 332, the dose rate of the radiation beam is measured by the first detector. At step 334, the dose rate of the radiation beam is measured by the second detector. However, the order of the measurements performed at steps 332 and 334 could be reversed, or the measurements of steps 332 and 334 could be made at the same time. The two measurements are then compared at step 336. If the dose rate determined from measurements at the first detector is not greater than the dose rate as determined from measurements at the second detector by a predetermined amount, no fault will be indicated 338 and the method returns to step 332. The property of the radiation beam is measured again so that the values are regularly monitored. If, however, the dose rate as measured by the first detector is greater than the dose rate as measured by the second detector by more than the predetermined amount, for example 20%, a signal is generated at step 340. This signal can be sent at step 342, for example, to the radiotherapy system control system 218. This signal can, for example, be used to deactivate the accelerator 220, preventing the production of further radiation. If such a signal is generated, it could be logged for diagnostic purposes, so that for example, a service engineer is more readily able to determine the cause of the fault condition or system shut down.

Monitor chambers of the type described above can be used to measure the dose of radiation delivered by the system. In addition, the chambers can be used in risk control measures to detect failures in beam transport. Such failures can lead to incorrect energy, profile shape (energy or tilt of beam) and absolute dose. In this respect, the ion chamber can be used to monitor the photon fluence shape. This gives an indication of the energy of the beam. While some systems do not experience change due to tilt (asymmetry in profile) as there is no way in normal operation that this would occur, in other cases a wrong bending magnet setting can cause a tilt (or wrong energy resulting in incorrect transport through bending system). The chamber can also be used to detect such failures.

Further changes can be made within the scope of the invention.

The invention claimed is:

1. An apparatus for measuring energy output of a radiation beam from a radiation beam source, the radiation beam having an axis, comprising:
   a first beam energy sensor at a first distance from the radiation beam source along the radiation beam axis;
   a second beam energy sensor located at a second distance from the radiation beam source along the radiation beam axis; and
   an energy absorbing layer located between the first and second sensors, and positioned such that radiation of the beam passing through the first sensor also passes through the energy absorbing layer before entering the second sensor, wherein each of the first and second beam energy sensors comprises:

a first electrode region configured, in use, to sample a central region of the radiation beam including the radiation beam axis; and a second electrode region at least partially surrounding the first electrode region and configured, in use, to sample a peripheral region surrounding but not including the central region, wherein the ratio of the areas of the first and second electrode regions of the first sensor is different from the corresponding ratio of the second sensor.

2. The apparatus as claimed in claim 1, wherein each sensor comprises a body defining a chamber, and upper and lower cover layers through which the radiation beam must pass for energy measurement; the energy absorbing layer being separate from the cover layers.

3. The apparatus as claimed in claim 1, wherein the energy absorbing layer is capable of absorbing at least 1% of the energy of the radiation beam passing from the first sensor to the second sensor.

4. The apparatus as claimed in claim 3, wherein the energy absorbing layer is capable of absorbing no more than 10% of the energy of the radiation beam passing from the first sensor to the second sensor.

5. The apparatus as claimed in claim 1, wherein the energy absorbing layer has an energy absorption that is at least that of 2 mm of stainless steel.

6. The apparatus as claimed in claim 1, wherein each sensor comprises an ion chamber.

7. The apparatus as claimed in claim 6, wherein each ion chamber comprises a body enclosing a signal electrode and polarising electrodes disposed on either side of the signal electrode.

8. The apparatus as claimed in claim 1, wherein the area of the first electrode regions of the first sensor is less than the area of the second electrode region of the first sensor.

9. The apparatus as claimed in claim 1, wherein the areas of the first and second electrode regions of the second sensor are approximately equal.

10. A radiotherapy system comprising a radiation generation system including an electron accelerator x-ray source for producing a beam of x-rays for treating a patient, and the apparatus as claimed in claim 1 positioned between the source and a treatment location of the patient.

11. The radiotherapy system as claimed in claim 10, further comprising a gantry on which the radiation generation system is mounted, the gantry being rotatable around the treatment location.

12. The radiotherapy system as claimed in claim 10, further comprising a magnetic resonance imaging system for imaging the patient at the treatment location during treatment with the beam of x-rays.

13. The radiotherapy system as claimed in claim 12, wherein the gantry is mounted for rotation through more than 360° around the treatment location.

14. A method of operating the radiotherapy system as claimed in claim 10, the method comprising:

operating the electron accelerator x-ray source to generate the beam of x-rays; and operating the apparatus for measuring radiation beam energy output from the source in accordance with the apparatus as claimed in claim 10.

15. The method as claimed in claim 14, further comprising automatically ceasing operation of the source when the determined change in beam energy exceeds a predetermined value.

16. A method of operating the apparatus as claimed in claim 1, the method comprising:

making, via the first beam energy sensor, a first beam energy measurement at a first time and at the first distance from the radiation beam source along the radiation beam axis;

making, via the second beam energy sensor, a second beam energy measurement at the first time at the second distance from the radiation beam source along the radiation beam axis, the second distance being greater than the first distance, and the beam having passed through the energy absorbing layer between the first and second distances;

making a third beam energy measurement at a second time at the first distance;

making a fourth beam energy measurement at the second time at the second distance, the beam having passed through the energy absorbing layer; and measuring changes between the first, second, third, and fourth beam energy measurements, and determining a change in beam energy from the first time to the second time using the measured changes, wherein:

the first and third beam energy measurements are made in a central region including the beam axis, and the second and fourth beam energy measurements are made in a peripheral region at least partially surrounding but not including the central region.

17. The method as claimed in claim 16, further comprising:

making a fifth beam energy measurement at the first time at the first distance, and a sixth beam energy measurement at the second time at the first distance, the fifth and sixth beam energy measurements being made in the peripheral region;

making a seventh beam energy measurement at the first time at the second distance, the beam having passed through the energy absorbing layer, and an eight beam energy measurement at the second time at the second distance, the beam having passed through the energy absorbing layer, wherein the seventh and eighth measurements are in the central region; and measuring changes between the first, second, third, fourth, fifth, sixth, seventh, and eighth beam energy measurements, and determining the change in beam energy from the first time to the second time using the measured changes.

* * * * *

UNITED STATES PATENT AND TRADEMARK OFFICE
CERTIFICATE OF CORRECTION

PATENT NO. : 11,052,266 B2
APPLICATION NO. : 16/276679
DATED : July 6, 2021
INVENTOR(S) : David Anthony Roberts et al.

It is certified that error appears in the above-identified patent and that said Letters Patent is hereby corrected as shown below:

On the Title Page

Item (30), delete "1802646" and insert --1802646.8--.

Signed and Sealed this
Nineteenth Day of July, 2022

Katherine Kelly Vidal
*Director of the United States Patent and Trademark Office*